United States Patent [19]
Johnston et al.

[11] Patent Number: 5,961,326
[45] Date of Patent: Oct. 5, 1999

[54] METHOD AND APPARATUS FOR PROTECTING AGAINST CROSS CONTAMINATION OF PATIENTS CAUSED BY ORAL REFLUX IN DENTAL INSTRUMENT WATER AND AIR LINES

[75] Inventors: Simon E. Johnston; Anna M. Johnston, both of Kirkland, Wash.; Jeffrey F. Williams, Mason, Mich.

[73] Assignee: SciTech Dental, Inc., Seattle, Wash.

[21] Appl. No.: 08/918,815

[22] Filed: Aug. 26, 1997

Related U.S. Application Data

[62] Division of application No. 08/551,343, Nov. 1, 1995, Pat. No. 5,709,545.

[51] Int. Cl.⁶ .................................................. A61G 17/02
[52] U.S. Cl. ................................................ 433/80; 433/82
[58] Field of Search ................................. 433/80, 81, 82, 433/83, 84, 85, 86, 87, 88, 89, 126, 114

[56] References Cited

U.S. PATENT DOCUMENTS

| | | | |
|---|---|---|---|
| 3,476,144 | 11/1969 | Krantz | 137/544 |
| 4,026,025 | 5/1977 | Hunt | 32/22 |
| 4,342,315 | 8/1982 | Jackson | 128/349 R |
| 4,797,098 | 1/1989 | Kawata | 433/98 |
| 4,818,258 | 4/1989 | Vann, III | 55/158 |
| 4,950,159 | 8/1990 | Hansen | 433/80 |
| 5,049,071 | 9/1991 | Davis et al. | 433/80 |
| 5,076,787 | 12/1991 | Overmyer | 433/95 |
| 5,192,206 | 3/1993 | Davis et al. | 433/80 |
| 5,204,004 | 4/1993 | Johnston et al. | 210/651 |
| 5,370,534 | 12/1994 | Wolf et al. | 433/80 |
| 5,464,397 | 11/1995 | Powers, Jr. | 604/246 |
| 5,474,451 | 12/1995 | Dalrymple et al. | 433/80 |

OTHER PUBLICATIONS

NSK America Corporation Advertisement for "Clean Head System" and "Non-Retraction Valve," headed "Good News Toward A Healthier Environment for Both Dental Care Providers and Receivers," 1 page.

*Primary Examiner*—Nicholas D. Lucchesi
*Attorney, Agent, or Firm*—Ronald M. Anderson

[57] ABSTRACT

A filter and one-way valve for protecting a dental patient from contamination by bacteria that may be picked up by water flowing through a supply line and to prevent cross contamination of patients from the reflux of fluid from inside a patient's mouth. Several different embodiments of the invention are disclosed, including a filter/one-way valve (38) that combines a filter (42) with a one-way valve (46) in an integral assembly. This assembly is installed in a water line (34) supplying water to an air/water syringe (20), or other dental instrument, such as a dental hand piece (160), or an ultrasonic scalar. Alternatively, a separate filter is installed in the water (and/or air) line upstream of the dental instrument, and a one-way valve (140) is installed between the head of the dental instrument and a tip through which water is injected into the mouth of a patient. Furthermore, an adapter (170) that couples to a bypass circuit in which the filter/one-way valve is installed enables the benefits of the present invention to be achieved with respect to the high-speed hand piece without cutting into a line (188) through which water and other fluids are supplied to the hand piece.

9 Claims, 6 Drawing Sheets

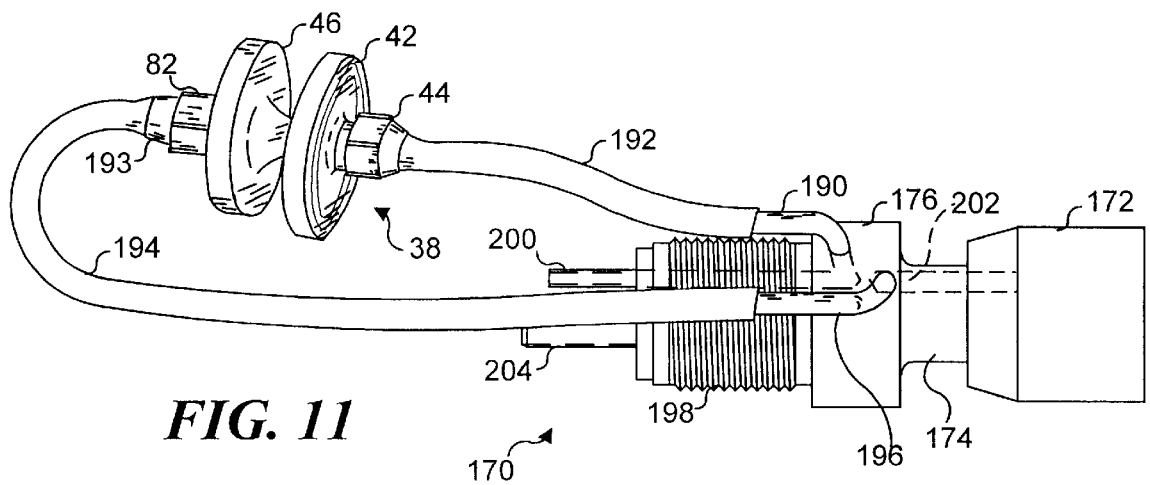
FIG. 11
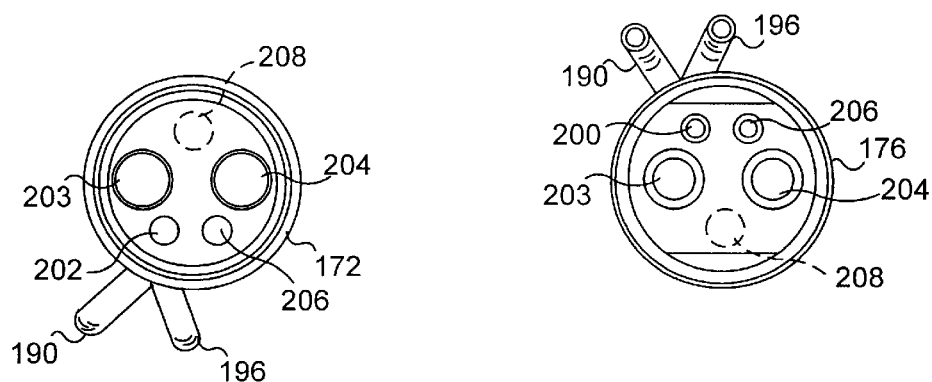
FIG. 12A  FIG. 12B
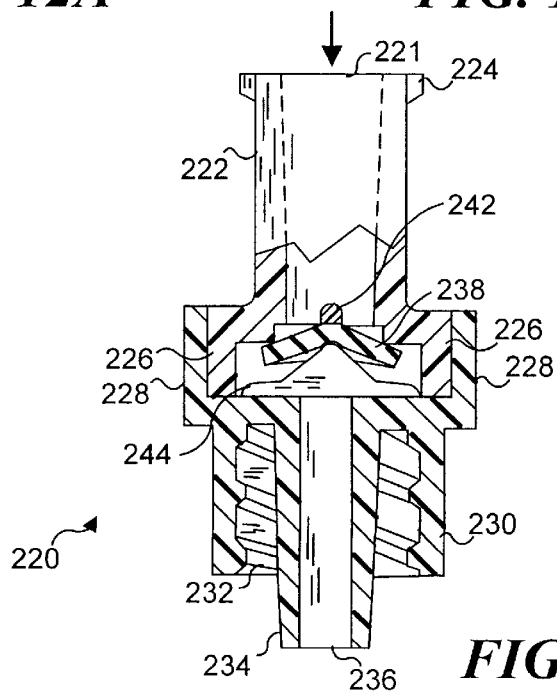
FIG. 13

METHOD AND APPARATUS FOR PROTECTING AGAINST CROSS CONTAMINATION OF PATIENTS CAUSED BY ORAL REFLUX IN DENTAL INSTRUMENT WATER AND AIR LINES

This application is a divisional application, based on prior application Ser. No. 08/551,343, now U.S. Pat. No. 5,709,545, filed on Nov. 1, 1995, the benefit of the filing date of which is hereby claimed under 35 U.S.C. § 120.

FIELD OF THE INVENTION

This invention generally pertains to preventing the cross contamination of dental patients by microbial agents within the lines carrying fluids to a dental instrument, and more specifically, to a method and apparatus that protect against oral reflux of such agents into the dental instrument during treatment of one patient and subsequent transfer to other patients treated with the dental instrument.

BACKGROUND OF THE INVENTION

The air/water syringe is a instrument commonly used by dentists for lavaging a patient's mouth to rinse away debris and for drying surfaces within the mouth during various dental procedures. During use, the tip of the syringe is inserted into a patient's mouth, and one or both selector valves on the hand piece of the syringe are activated to inject a stream of water and/or compressed air. When the operator releases the selector valve(s), fluid flow from the syringe tip is interrupted. However, fluid can flow back into the syringe from inside the mouth of the patient. This fluid is likely to carry microbes, which will be drawn into the passages at the tip of the syringe and further upstream, into the head and internal passages of the syringe. Even if the tip is replaced or sterilized between patients, the microbes within the syringe passages can infect patients who are subsequently treated. The problems can also arise in other types of dental instruments, such as high-speed hand pieces.

In recognition of this potential hazard, some manufacturers have installed check valves within the dental console or within the heads or handles of some models of dental instruments. Yet, such check valves, which are not intended to be replaced or maintained on a regular basis, can easily leak or fail completely; the failure is not evident and is difficult to detect. Even if a check valve is fully operational, capillary force developed in the small diameter lumens that extend through the dental instrument can cause aerosols or liquids from within the patient's mouth to be drawn back into the device. In certain syringe models, when the flow is interrupted by the selector valves, the movement of the valve creates a slight negative pressure pulse that can draw fluids back into the syringe tip. Turbulent fluid flow through a dental instrument can cause low pressure eddies that collapse once the flow is interrupted. Collapse of a low pressure eddy can create a negative pressure pulse that sucks fluid back into the internal passages of the instrument.

Although dentists commonly sterilize dental instruments and use disposable syringe tips and other components that are changed between patients, patients may not be protected against cross contamination caused by oral reflux. Fluid within the mouth of a patient who is undergoing dental surgery or even a simple cleaning often contains blood. If the blood and other fluids from within the patient's mouth are drawn into a syringe tip or inside the fluid passages of a hand piece, microbial contamination carried by the fluid can reach components of the instrument that are not sterilized or replaced between patients and the contaminants can be drawn back into the dental water lines. Subsequent patients, on which the instrument is used, are then exposed to the contamination carried by air/water from inside the instrument and the water lines, even if conveyed through an otherwise sterile tip. Moreover, patients subsequently treated may have water and/or air from the contaminated instrument or water lines injected into open wounds within their mouths.

The cross contamination problem can have serious medical consequences, particularly if the microbial contaminants include the HIV virus. Unfortunately, most dentists are unaware that the steps commonly taken to prevent cross contamination are inadequate to deal with oral reflux.

Another related problem arises from the contamination of air and water as these fluids flow through delivery lines from a dental console. The fluid lines that couple the dental console to the syringe or other dental instrument are subject to the growth of a biofilm on their inner surfaces; the biofilm serves as source of possibly pathogenic bacteria that contaminate the fluids flowing through the lines. A solution to this part of the problem is disclosed in commonly assigned U.S. Pat. No. 5,204,004 (Johnston et al.). In this prior patent, an in-line filter is installed in the water line conveying water to a dental syringe or other instrument, just upstream of the instrument. The downstream section of line is bacteriologically sterile. The filter includes a microporous membrane having a porosity selected to block a predefined size of particulate matter, including bacteria, without significantly restricting water flow. Bacteria released from any biofilm within the water line installed upstream of the filter are thus prevented from reaching a patient's mouth. However, the in-line filter cannot prevent oral reflux cross contamination when used without an operative check valve that is disposed in a position close to the dental instrument.

Clearly, it would be desirable to prevent cross contamination of dental patients due to oral reflux and to ensure that steps taken to prevent cross contamination by changing disposable syringe tips between patients are truly effective. Currently, there is no available solution to the problem or even a clear recognition that the problem is not adequately corrected by check valves built into the dental consoles or dental instruments.

SUMMARY OF THE INVENTION

In accordance with the present invention, apparatus are defined for preventing a contaminated fluid from entering a patient's mouth through a dental instrument having a fluid passage through which fluid is injected into the patient's mouth. The apparatus includes a housing having an inlet port and an outlet port, and the housing is adapted for coupling in fluid communication with the dental instrument so that the apparatus is easily replaceable. Means are provided for bacteriological sterilization of a fluid flowing through the housing. These means include a microporous membrane having a porosity selected to block a predefined size of particulate matter, including bacteria, without substantially restricting fluid flow through the membrane. The membrane is disposed within the housing between the inlet port and the outlet port and sealed within the housing so that the fluid flowing through the inlet port passes through the membrane before flowing out the outlet port. A one-way valve is also disposed within the housing between the inlet port and the outlet port. The one-way valve permits any fluid entering through the inlet port to flow through the membrane and out the outlet port, but blocks fluid flow in an opposite direction.

The one-way valve and the membrane thus cooperate to prevent the contaminated fluid from entering the patient's mouth through the dental instrument and to prevent the dental instrument from becoming contaminated by an oral reflux from inside the patient's mouth.

In one embodiment, the housing further includes a quick-connect inlet fitting on the inlet port and a quick-connect outlet fitting on the outlet port. The housing may thus be adapted for installation in a fluid line, upstream of the dental instrument, so that the fluid flowing through the housing is supplied to the dental instrument free of bacterial contamination. The one-way valve then prevents the oral reflux of the contaminated fluid from inside a patient's mouth back into the fluid passage of the dental instrument.

In another embodiment, the fluid passage is within a disposable tip for the dental instrument. In this case, the input port of the housing is adapted to couple to the dental instrument, between the dental instrument and the fluid passage. Fluid passing into the fluid passage first flows through the membrane and the one-way valve, thereby preventing bacteria from entering the fluid passage from the dental instrument and preventing the oral reflux of the contaminated fluid from inside the patient's mouth into the fluid passage. Optionally, the housing is formed integrally with the disposable tip and is discarded after being used with a patient. The fluid flowing through the housing typically comprises water, but may alternatively comprise compressed air.

Preferably, the one-way valve comprises a generally planar sheet of an elastomeric material having a first and second opposed surfaces, and a peripheral ridge formed in the housing against which the first surface of the sheet of elastomeric material seals.

The apparatus also includes an adapter for the dental instrument. This adapter has an inlet port through which the fluid flows into the adapter; an outlet port through which fluid is conveyed into the dental instrument from the adapter; and a bypass fluid circuit in which the housing is disposed. The bypass circuit conveys the fluid entering the inlet port to the one-way valve and conveys the fluid flowing through the means for bacteriological sterilization to the outlet port of the adapter.

Another aspect of the present invention is directed to a method for preventing a contaminated fluid from entering a patient's mouth through a dental instrument, said dental instrument having a fluid passage through which fluid is injected into the patient's mouth. The method includes steps that are generally consistent with the functions of the elements comprising the apparatus discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 11 is a side view of the adapter and of the integral filter and one-way valve;

FIGS. 12A and 12B are end views of the output and input ports, respectively, of the adapter; and FIG. 13 is a partial cut-away view of an alternative one-way valve for use in the present invention.

DESCRIPTION OF THE PREFERRED EMBODIMENT

Figure 1:
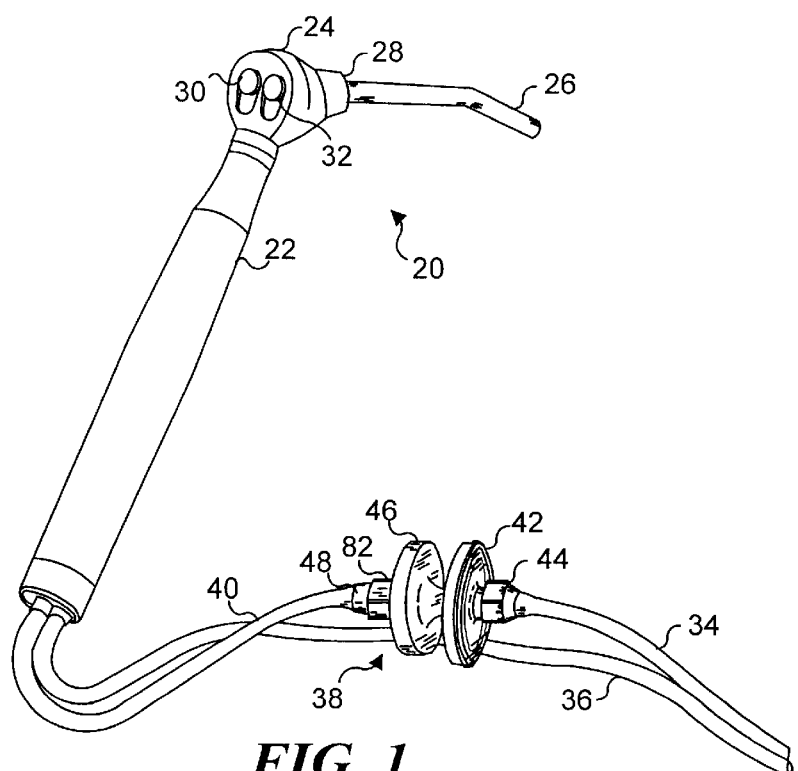
FIG. 1 is an isometric view of a dental air/water syringe showing a first embodiment of the present invention installed in a water supply line.

An integral filter/one-way valve 38 intended for installation in a water line 34, for conveying water from a dental console source (not shown), to an air/water syringe 20 is shown in FIG. 1. The syringe, which enables air and/or water to be selectively injected into the mouth of a patient (not shown), includes a handle 22, a head 24, and a tip-holding collar 28, which is threaded into head 24 and includes an internal compression fitting used to attach a tip 26. Air and water are respectively supplied to the syringe through an air line 36 and water line 34. Head 24 of the syringe includes two valves for controlling the flow of air and water into tip 26 by actuating slider buttons 30 and 32, respectively. Syringes of this type are well known to those of ordinary skill in the art, and further details need not be disclosed in connection with the present invention.

To install combination filter/one-way valve 38 in water line 34 in a retrofit operation, the line is cut approximately four to six inches upstream of its point of entry into handle 22 of air/water syringe 20. A female Luer fitting 44 is installed on the upstream end of water line 34 at the point where the line was cut, and a corresponding male Luer fitting (not shown) is installed on the cut end of a short length 40 of the water line, which remains connected to handle 22, after the line is sterilized with an appropriate sterilizing solution. Alternatively, the short length of water line can be replaced at the time the integral filter/one-way valve is installed, using a short section of pre-sterilized tubing.

Water flowing through water line 34 initially passes through a filter 42, and then through a one-way valve 46 comprising integral filter/one-way valve 38. It is also contemplated that instead of being retrofitted to an existing water line, integral filter/one-way valve 38 might be included in a complete replacement air and water line assembly for use in connection with a dental instrument such as syringe 20. In this case, an existing syringe could be fitted with a new air and water line that includes integral filter/one-way valve 38, as an alternative way to provide the benefits of the present invention.

As explained in commonly assigned U.S. Pat. No. 5,204,004, a biofilm tends to grow on the internal surface of water lines, and this biofilm can contaminate water flowing through the lines with bacteria, which are then injected into a patient's mouth during use of a dental instrument that is supplied with water through the line. Introduction of such bacteria into the patient's mouth after a dental procedure is performed on the patient that causes intra-oral bleeding can enable the bacteria to enter the patient's bloodstream, and may subsequently lead to illness caused by the bacteria. However, after installation of filter 42, bacteria carried by the water flowing through water line 34 are substantially blocked, so that the bacterial count in water flowing through short section 40 of the water line, and through syringe 20 into the patient's mouth is sufficiently low to justify labeling the water as "sterile," consistent with the accepted medical definition of that term. Accordingly, a patient receiving water intra-orally through tip 26 after installation of filter 42 is protected from any significant introduction of bacteria from a biofilm in the relatively longer upstream section of water line 34. As a result, the risk of bacterial contamination due to bacteria in the water stream introduced into the patient's mouth during dental procedures is virtually eliminated.

Further, one-way valve 46 prevents retraction or reflux of fluid from inside a patient's mouth, which could contaminate the interior passages of tip 26 and the interior passages of head 24. As noted above, even if tip 26 is replaced between patients and syringe 20 is cleaned, tests have shown that bacteria and viruses may remain alive within the interior passages of syringe 20 and subsequently be transmitted to a different patient with which the syringe is used.

If an anti-retraction valve were permanently mounted within the head of the syringe at the time of its manufacture, it might initially prevent reflux of fluids into tip 26 from inside a patient's mouth; however, since anti-retraction valves that are sometimes built-into the heads of high-speed dental hand pieces often fail after being in use for a period of time, an anti-retraction valve permanently installed in head 24 of syringe 20 would also very likely fail after a time and then become ineffective in preventing cross contamination of patients. Accordingly, provision of filter/one-way valve 38 in water line 34 both prevents bacterial contamination of a patient from the biofilm growing inside water line 34 and prevents the reflux of fluid into tip 26, which might contaminate the dental instrument and contaminate other patients when subsequently used with them. Filter/one-way valve 38 is relatively low in cost and is therefore easily replaced on a regular basis, even between patients if desired, insuring that the one-way valve is always operational. Although FIG. 1 illustrates the present invention in use with air/water syringe 20, it is also contemplated that the filter/one-way valve be installed in the air/water lines conveying these fluids to other types of dental instruments, including a dental hand piece, or an ultrasonic scalar.

Figure 2:
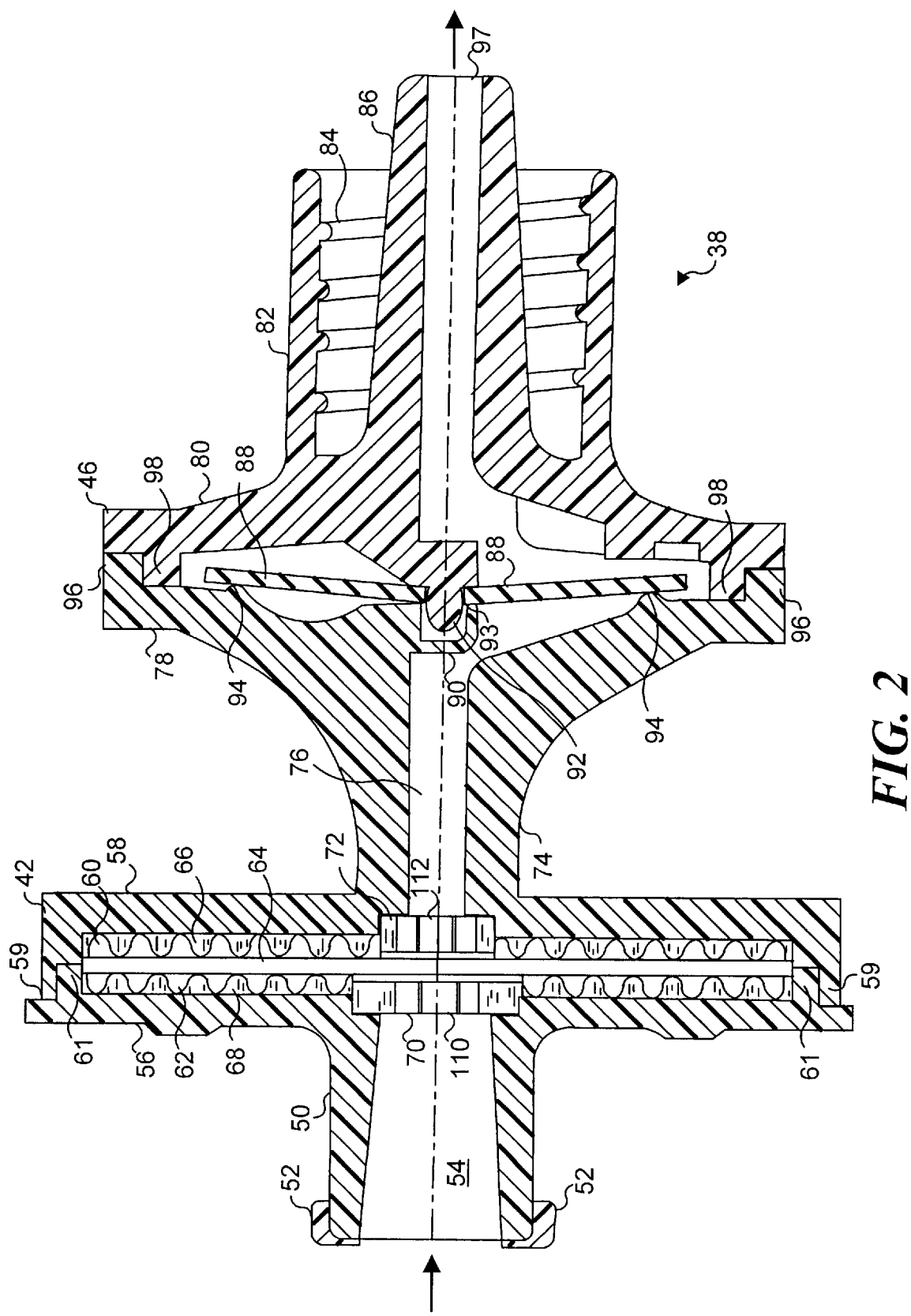
FIG. 2 is a cut-away elevational view of an integral filter and one-way valve assembly in accordance with the first embodiment of the present invention.

Details of the internal construction of filter/one-way valve 38 are shown in FIG. 2. The housing of the filter/one-way valve is made of injection-molded plastic components. In regard to the orientation shown in FIG. 2, water enters an inlet port 50 on the left of filter 42 and flows through an internal passage 54. Ribs 52, which are disposed on opposite sides of inlet port 50, configure the inlet port as a male Luer fitting and adapt it to couple with a female Luer fitting (not shown).

The housing includes a filter inlet cover 56, which extends radially outward from inlet port 50 and is bonded to a filter outlet cover 58. The filter inlet cover includes an annular ring 61 that is slightly inset from its outer perimeter and is sized to fit within a corresponding annular ring 59 on filter outlet cover 58. After installation of a microporous membrane 64 between the filter inlet and outlet covers, a suitable adhesive or ultrasonic bonding is used to join these two components of the housing and to provide a fluid-tight seal.

Figure 5A:
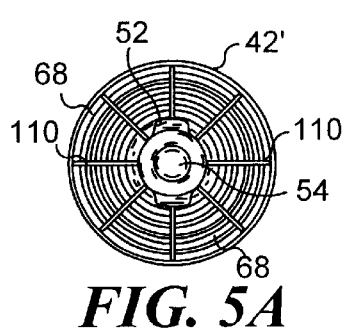
FIGS. 5A and 5B are elevational views of the inlet port and outlet port, respectively, of the filter in FIG. 3.

Microporous membrane 64 has a porosity that blocks the passage therethrough of particulate matter having a diameter larger than approximately 0.2 microns. The microporous membrane is sealingly disposed between filter inlet cover 56 and filter outlet cover 58, so that its surface on the side facing toward inlet port 54 is exposed to concentric passages 62. Passages 62 are in fluid communication with a deflector 70 that directs fluid passing through inlet port 50 radially outward into concentric passages 62. The concentric passages are defined by a plurality of spaced-apart ridges 68 disposed on the inner face of filter inlet cover 56. On the outlet surface of the microporous membrane, concentric passages 60 are defined by spaced-apart annular ridges 66, which are formed on the inner face of filter outlet cover 58. Fluid passing through the inlet port is dispersed into radial passages 110 by deflector 70. FIG. 5A shows how radial passages 110 are spaced apart around the inlet port at approximately 45° intervals in a filter 42', which is generally similar to filter 42, but not combined with one-way valve 46.

Figure 5B:
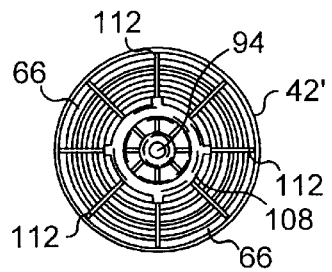

In a similar manner, the fluid passing through the microporous membrane travels through concentric passages 60 to radial passages 112, which are also disposed at 45° increments within the inner face of filter outlet cover 58. (See filter 42' in FIG. 5B.) As shown in FIG. 2, a deflector 72 directs fluid from radial passages 112 into an internal passage 76 that conveys fluid into one-way valve 46, and which is aligned along the longitudinal axis of filter/one-way valve 38.

Although FIG. 1 shows filter/one-way valve 38 installed in a water line, it may also be installed in air line 36. In this case, the installation would be generally as described above in connection with water line 34. However, for use in an air line, microporous membrane 64 would be coated with a hydrophobic coating, excluding water from passing through the membrane. The microporous membrane would also prevent bacteria from entering the compressed air passages of the syringe, and the one-way valve would prevent reflux of air and other fluids back into the air passages of the syringe (or other dental instrument with which the present invention is used) from inside a patient's mouth.

On filter/one-way valve 38, one-way valve 46 is integrally connected to filter 42 via a radially diverging neck section 74 of the housing through which internal passage 76 extends. The outer surface of neck section 74 curves radially outward from its connection to filter outlet cover 58 to form a housing section 78 for one-way valve 46. An annular ridge 96 that runs around the perimeter of the neck section is bonded to a corresponding annular ridge 98 formed on a housing section 80 of the housing. Annular ridges 96 and 98 are adhesively bonded together using a suitable adhesive, or ultrasonically bonded, as is well known to those of ordinary skill in the art, forming a fluid-tight seal. Before one-way valve 46 is thus assembled, an elastomeric disk 88 is mounted inside the housing to control fluid flow through the one-way valve, by inserting a round projection 92 through a slightly smaller opening 93 that is formed in the center of the elastomeric disk. Once annular ridges 96 and 98 are joined together to assemble the housing, the elastomeric disk is held in place by a shoulder 90 formed on the inside of housing section 78, the shoulder also provides a fluid-tight seal between the housing and elastomeric disk 88 around projection 92.

An annular sealing ridge 94 extends around the inner surface of the neck section of the housing for one-way valve 46. Since one-way valve 46 is a normally closed valve, the facing (upstream) surface of elastomeric disk 88 normally seals against the annular sealing ridge in response to inherent spring force of the elastomeric disk. The seal between elastomeric disk 88 and annular sealing ridge 94 thus prevents backflow through one-way valve 46. However, in response to fluid pressure within internal passage 76 acting upon the upstream surface of elastomeric disk 88, the disk is deflected away from sealing ridge 94, permitting fluid to flow past the elastomeric disk and into an outlet passage 97. Outlet passage 97 is disposed inside a nozzle portion 86 of a female Luer fitting 82. A plurality of helical threads 84 are formed around the inner surface of the female Luer fitting, enabling the outlet port of one-way valve 46 to be coupled to a corresponding male Luer fitting (not shown in this Figure).

Figure 3:
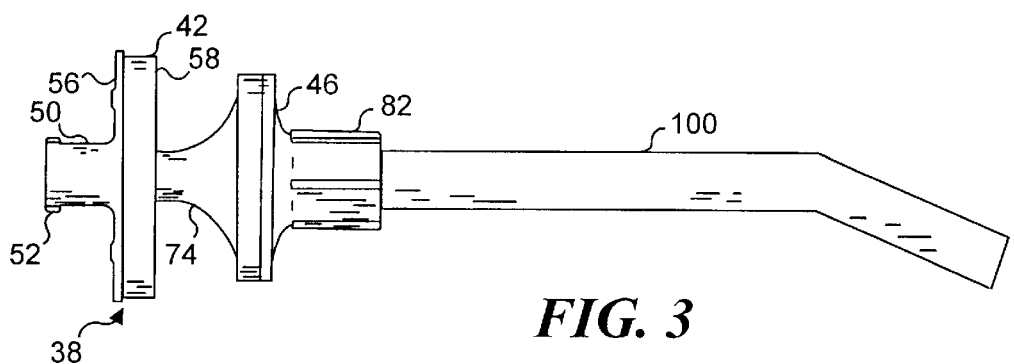
FIG. 3 is an elevational view of a second embodiment of the present invention, installed on a syringe tip.

It is also contemplated that filter/one-way valve 38 might alternatively be connected to the inlet of a tip 100 as shown in FIG. 3. The inlet port of the filter/one-way valve would then be coupled to a head portion of a water-only syringe (not shown). An appropriate adapter, e.g., one including a Luer fitting, would be required to couple the inlet port of filter 42 to the head portion of such a syringe. However, mounting filter/one-way valve 38 between the syringe and tip 100 might provide an advantage, compared to the embodiment shown in FIG. 1, since it is generally preferable to locate one-way valve 46 as close as possible to the outlet of the tip to minimize the reflux of water and oral fluids into the passages in the tip from inside a patient's mouth.

Figure 4:
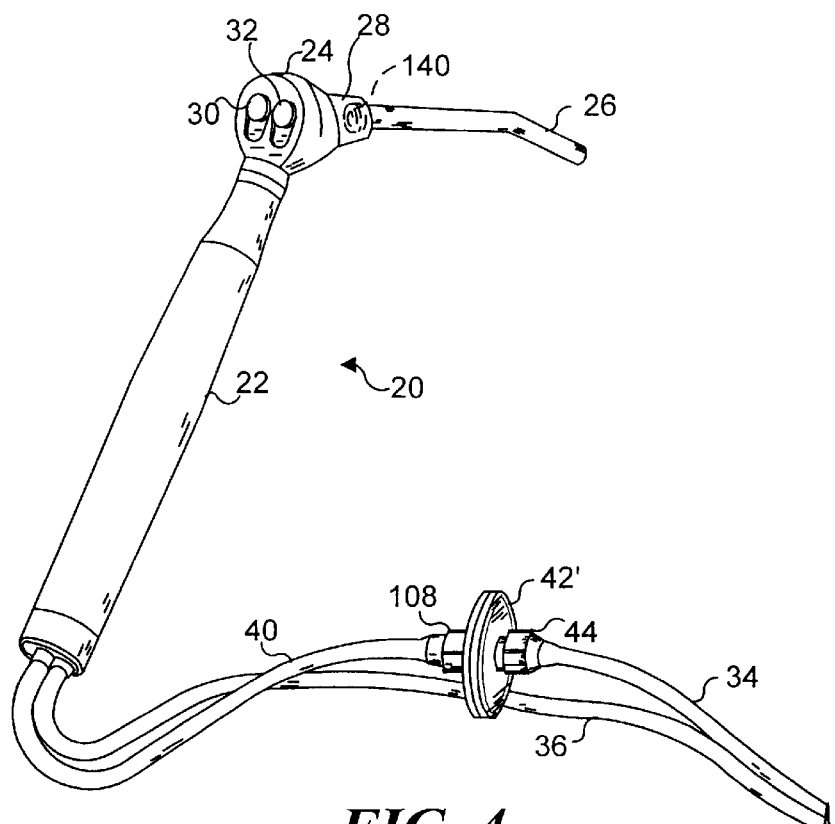
FIG. 4 is an isometric view of a syringe, showing a filter installed upstream of the air/water syringe handle and a one-way valve that is integral with a tip disposed downstream of the syringe head.

In FIG. 4, yet a further alternative is shown, wherein the filter and one-way valve are split into two separate components, including a filter 42' that is disposed in water line 34 (or in air line 36) as described above, and a one-way valve 140 (shown in detail in FIG. 9) that is coupled to tip 26. Tip 26 and one-way valve 140 are connected to the syringe by collar 28, inside of which is disposed the compression fitting that holds the tip in place on the head of the syringe.

Filter 42' is modified to include a female Luer fitting 108 that connects to a corresponding male fitting (not shown) installed on the upstream end of tubing 40. Internally, filter 42' comprises microporous membrane 64, disposed between inlet housing cover 56 and an outlet housing 58'. Details of filter 42' are shown in FIG. 8.

Figure 8:
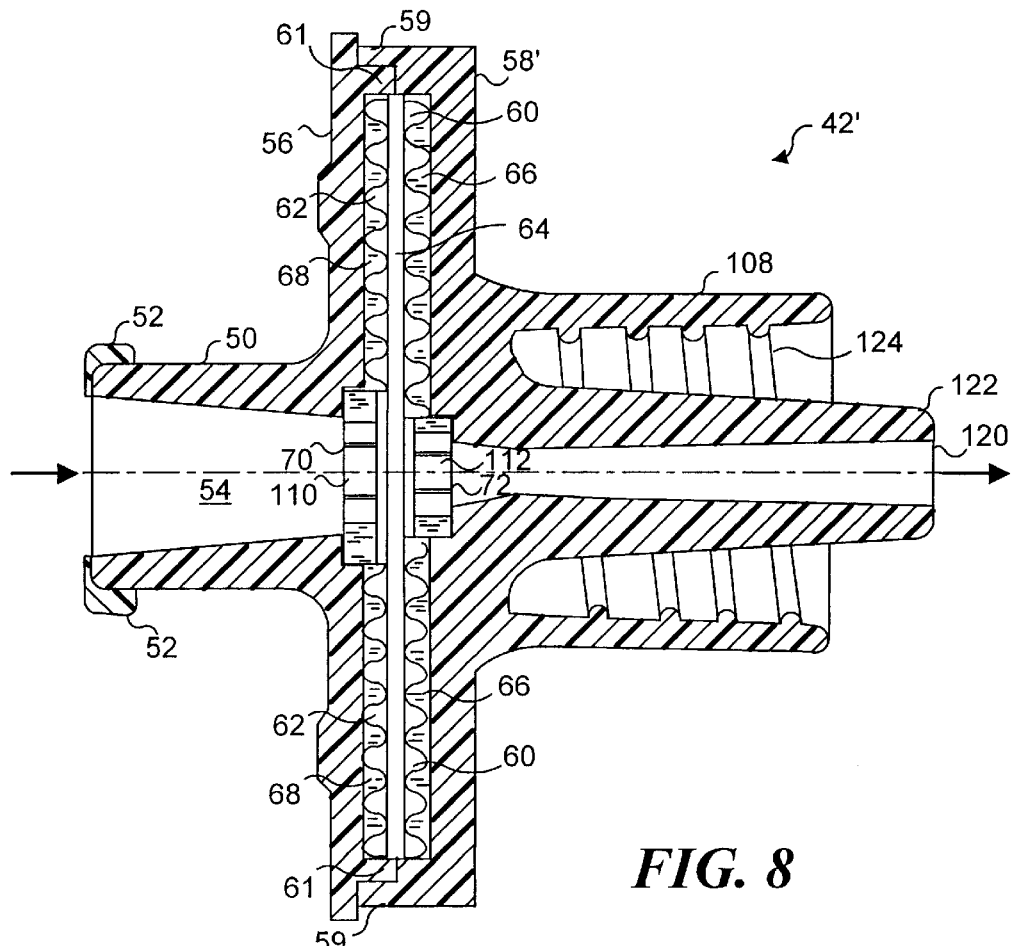
FIG. 8 is a cut-away elevation view of the filter shown in FIG. 4.

FIG. 8 illustrates a cross-sectional view of filter 42'. By comparison of FIG. 8 with FIG. 2, it will be apparent that the internal structure of filter 42 is virtually identical to that of filter 42', in regard to the path followed by fluid flowing through the microporous membrane. However, as shown in FIG. 8, the outlet side of filter 42' includes a nozzle 122 of female Luer fitting 108. Disposed around nozzle 122 on the inside surface of Luer fitting 108 is a helical thread 124. Fluid passing through microporous membrane 64 thus exits through a passage 120 that extends longitudinally through nozzle 122.

Figure 9:
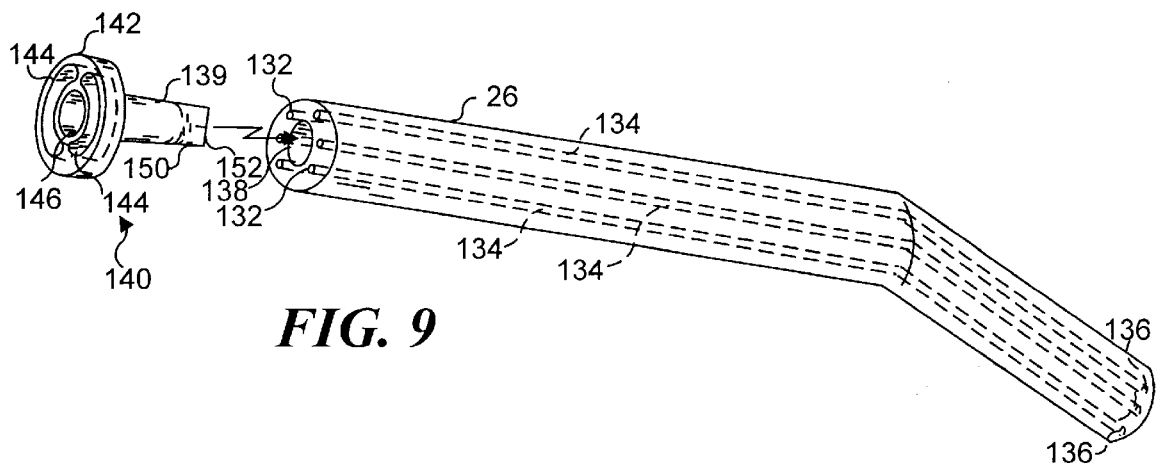
FIG. 9 is an exploded isometric view of a duck-bill one-way valve and syringe tip.

With reference to FIG. 9, it will be noted that one-way valve 140 is of a substantially different design than one-way valve 46. An advantage of one-way valve 140 is that it is installed in an opening 138 at the inlet of tip 26, providing greater protection against reflux of fluid from within a patient's mouth. Tip 26 and one-way valve 140 are preferably disposable and are replaced between patients. Alternatively, tip 26 may be autoclaved after use with each patient and only the one-way valve replaced at regular intervals or before the tip is used with the next patient.

At its upstream end, tip 26 includes a plurality of small openings 132 that are spaced apart circumferentially around opening 138, in fluid communication with passages 134. Passages 134 extend through the length of tip 26 to corresponding openings 136, which are disposed at the downstream end of tip 26, and convey compressed air into the patient's mouth. Tip 26 is mounted to syringe 20 using a compression fitting (not shown) that locks the tip to the head of the syringe and seals it in place.

One-way valve 140 is made from an elastomeric material, as is common of one-way valves of this type. A duck-bill portion 150 extends from the downstream end of a tubular portion 139 and is generally flat, compared to the tubular portion. The duck-bill portion includes a slit 152 in fluid communication with a passage 146 that extends inside tubular portion 139. Water readily flows through passage 146, through duck-bill portion 150, and into a central water passage within tip 26 through opening 138. However, reflux of contaminated fluid back into the central water passage of tip 26 from a patient's mouth is prevented, since the natural elasticity of the duck-bill portion closes slit 152 to prevent fluid from flowing back through duck-bill portion 150 toward head 24 of syringe 20.

A flange 142 on one-way valve 140 has a diameter slightly greater than that of tip 26. Moreover, a two arcuate passages 144 extend through flange 142 and are disposed circumferentially around passage 146 so as to overlie openings 132, thereby enabling compressed air to flow through one-way valve 140 and into passages 134 of tip 26 from head 24. Rotation of one-way valve 140 within opening 138 is not critical, since most of small openings 132 will be aligned with arcuate passages 144, regardless of the rotation position of the one-way valve.

Figure 6:
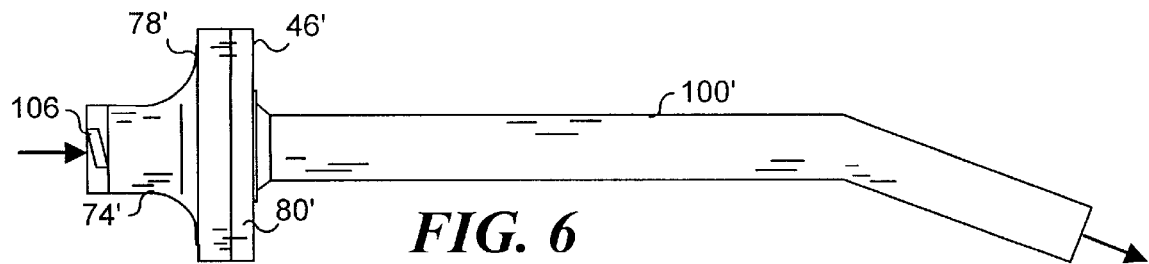
FIG. 6 is an elevational view of the integral one-way valve and tip shown in FIG. 4.

FIG. 6 shows a one-way valve 46' that is integrally formed with a tip 100' for use with a water-only syringe (not shown). Partial threads 106 extend radially outward from the inlet port of one-way valve 46', defining a male Luer fitting that enables it to be coupled to a female Luer fitting on an adapter (not shown) used to connect the one-way valve and tip to the head of the syringe. One-way valve 46' is thus modified relative to one-way valve 46, to include a neck section 74' extending from the male Luer fitting to form a housing 78'. Housing section 78' is coupled to an opposed housing section 80' to encapsulate elastomeric disk 88. The internal components of one-way valve 46' are generally identical to those of one-way valve 46. Housing 80' is further modified so that its outlet is directly connected to tip 100', forming an integral assembly. Accordingly, tip 100 and one-way valve 46' are designed to be used with a single patient and then discarded, to be replaced by another such assembly.

Figure 7:
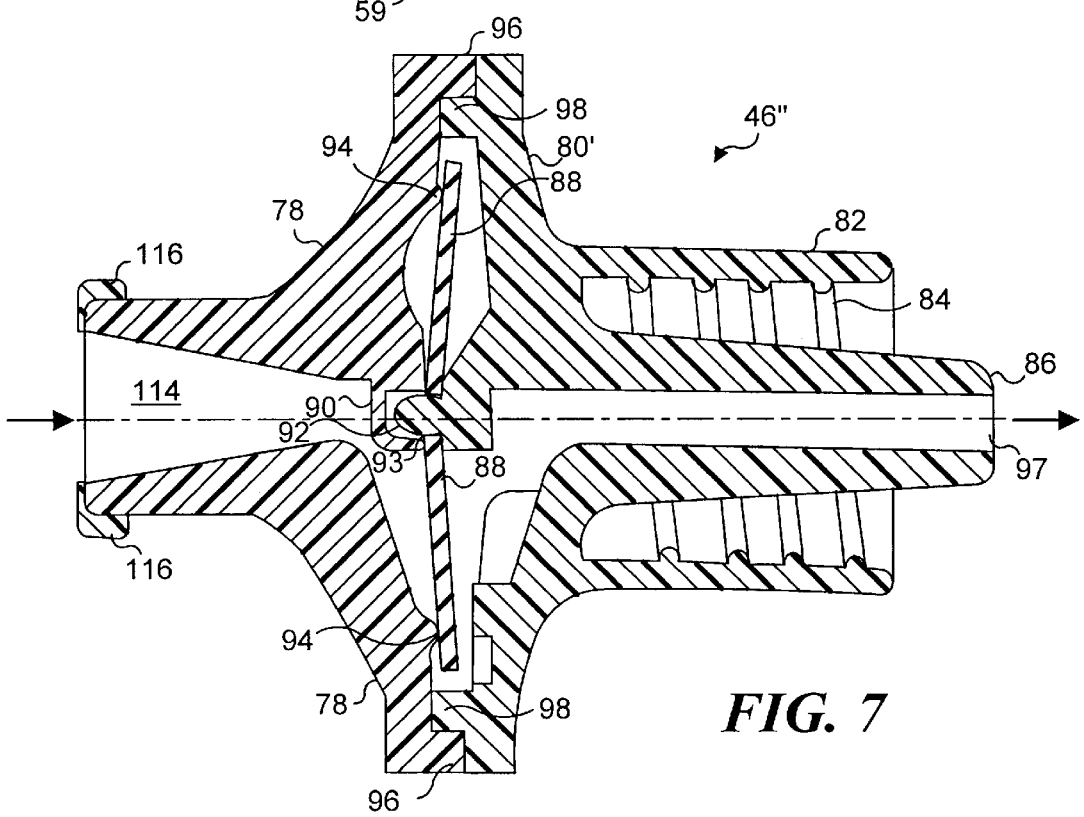
FIG. 7 is a cut-away elevational view of a one-way valve for use in the present invention.

FIG. 7 illustrates a one-way valve 46" that is similar to one-way valve 46', but which includes Luer fitting 82 like one-way valve 46. An inlet port 114 is provided for one-way valve 46" that includes Luer threads 116, for mating with a corresponding female Luer fitting. It should be noted that filter 42' and one-way valve 46" can be coupled together by connecting Luer fitting 108 to the inlet port of one-way valve 46", and rotating the one-way valve to engage threads 116 with threads 124. Thus, instead of using the integral assembly comprising filter/one-way valve 38, a combination of filter 42' and one-way valve 46" can be used in water line 34 (or air line 36), generally as shown in FIG. 1. It is also contemplated that tip 100' can be adapted to include a male Luer fitting on its upstream end, enabling it to be coupled to the Luer fitting at the output port of one-way valve 46", for use instead of one-way valve 46'. Thus, it may be possible to use a fresh tip 100' with each patient, and to change one-way valve 46" less frequently, thereby minimizing the cost of the protection afforded by the one-way valve.

Figure 10:
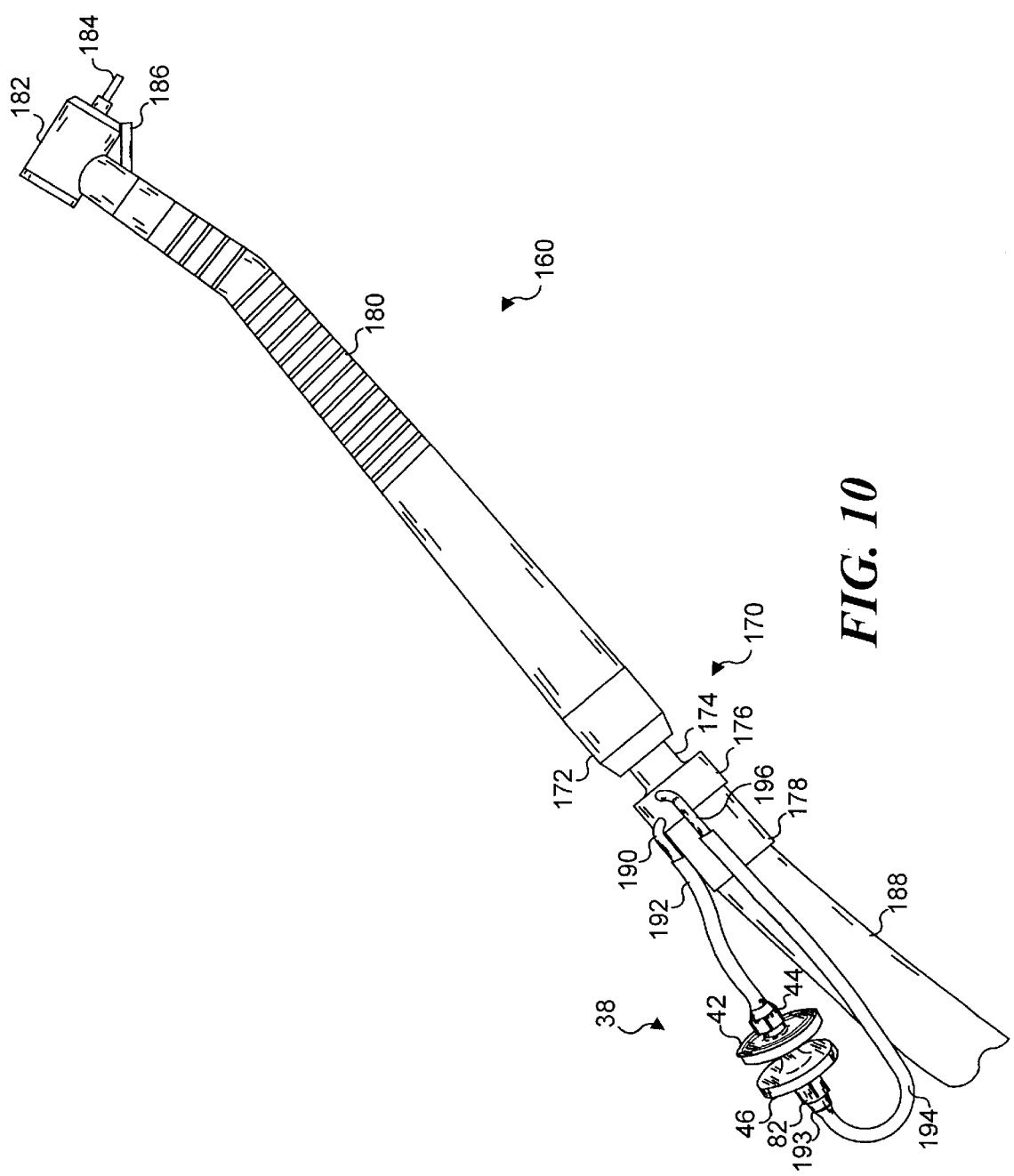
FIG. 10 is an isometric view of a high-speed dental hand piece with an adapter that diverts water flow through the integral filter and one-way valve and then back into the hand piece.

In FIG. 10, a dental hand piece 160 is shown that is fitted with an adapter 170 incorporating filter/one-way valve 38 to filter bacteria from the water flowing into a patient's mouth in which the hand piece is being used. One-way valve 46 also prevents reflux of fluid from the patient's mouth back into the internal passages of the hand piece.

Hand piece 160 is of generally conventional design, including a handle 180, a head 182 that includes a high-speed pneumatic motor (not shown), a drill 184, and an optional fiber optic light emitting port 186. Although not shown, head 182 includes a water passage through which cooling water is injected into a patient's mouth to cool a work site. High-pressure compressed air, return air, and water are conveyed through a line 188, that includes a plurality of passages (not separately shown in FIG. 10). A coupler 178 that is part of the hand piece normally attaches directly to the lower end of handle 180, providing a fluid-tight connection with the various passages in line 188 with corresponding internal passages within handle 180. Clearly, as mentioned above, it would be possible to retrofit filter/one-way valve 38 into the water and/or air passages of line 188 by cutting into the line as described above. Alternatively, a replacement line (not shown) for line 188 could be provided in which the filter/one-way valve are already installed. However, in the embodiment shown in FIG. 10, adapter 170 is inserted between coupler 178 and handle 180 to provide a bypass circuit enabling filter/one-way valve 38 to be inserted in the water (and/or air) path without cutting into line 188 or replacing it.

Details of adapter 170 are shown in FIG. 11, and in the end views of FIGS. 12A and 12B. Adapter 170 includes an internally threaded sleeve 172 that is rotatable around a neck 174 to couple adapter 170 to the lower end of handle 180 on dental hand piece 160. Neck portion 174 connects with a section 176. Water flows from inside the adapter out into the bypass fluid circuit through a tube 190. After passing through filter/one-way valve 38, the water returns from the bypass fluid circuit through a tube 196 to proceed upwardly through an internal passage 202 within neck portion 174, and on through the hand piece into the patient's mouth. As shown in FIG. 11, tube 190 of adapter 170 is coupled through a short section of flexible tubing 192 to Luer fitting 44, which connects to filter 42. Luer fitting 82 on one-way valve 46 is connected to a corresponding male Luer fitting 193 on one end of a short section of flexible tubing 194, and the opposite end of tubing 194 is coupled to tube 196. Thus, water flowing to dental instrument 160 through line 188 flows out into the bypass fluid circuit through tube 190, through flexible tubing 192, passes through filter 42, which removes any bacteria contained within the water, and then passes through one-way valve 46, and into flexible tubing 194. The water returns through flexible tubing 194 into tube 196 and flows into an internal passage 202, which conveys the water into handle 180 of dental hand piece 160. Water entering the patient's mouth is thus free of bacteria, and due to the presence of one-way valve 46, reflux of fluid back into the hand piece is prevented.

Adapter 170 includes a tube 203 that extends longitudinally through the adapter to convey high-pressure compressed air to drive the pneumatic motor in the dental hand piece and a tube 204 for conveying air back to the compressor after it is passed through the pneumatic motor. In addition, a tube 206 extends longitudinally through the adapter and is used for conveying cooling air to the work site within the patient's mouth. Optionally, an optical fiber 208 extends through the adapter, conveying light from an external high-intensity source (not shown) that passes through an optical fiber (not shown) within line 188, to illuminate the work site in the patient's mouth.

FIG. 13 discloses yet another embodiment for a one-way valve 220, of a design that is sold by Burron Medical Inc. This embodiment can also be incorporated into an integral filter/one-way valve similar to filter/one-way valve, which is shown in FIG. 2. One-way valve 220 includes an inlet port 221 comprising a male Luer fitting 222, which includes threads 224 on its outside circumference. Inlet port 226 is in fluid communication with an elastomeric disk 238. The elastomeric disk is supported between a cross bar 242 and a cross member 244, which cooperatively hold it in place so that it seals against a circumferential shoulder 226 on the inside of a housing 228. Elastomeric disk 238 is deflected by fluid flow to break this sealing contact between elastomeric disk 238 and shoulder 226, enabling fluid to flow past cross member 244 and into a female Luer fitting 230. The female Luer fitting is of generally conventional design, including a nozzle 234 through which a passage 236 extends, and threads 232 for engaging a corresponding male Luer fitting. One-way valve 220 can be used in place of one-way valves 46' or 46", as described above.

Although the present invention has been described in connection with several preferred embodiments, those of ordinary skill in the art will understand that many other modifications can be made thereto within the scope of the claims that follow. Furthermore, it must again be emphasized that the present invention is intended for use with any dental instrument that is supplied a fluid that is injected into the mouth of a dental patient. It should not be necessary to disclose the details of how the invention is used with each type of dental instrument. Thus, for example, there are not drawings of an ultrasonic scalar showing how the filter/one-way valve would be installed in the water line to this device. However, it will readily be apparent from the preceding description how the invention can thus be employed. Accordingly, it is not intended that the scope of the invention in any way be limited by the above description, but instead be determined entirely by reference to the claims that follow.

The invention in which an exclusive right is claimed is defined by the following:

1. Apparatus for preventing a contaminated fluid from entering a patient's mouth through a dental instrument, said dental instrument having an outlet through which fluid is injected into the patient's mouth, said apparatus comprising:

(a) housing means having at least one inlet port and at least one outlet port, said housing means being adapted to couple in fluid communication with the dental instrument so that the fluid flows through the housing means before being injected into the patient's mouth;

(b) a quick-connect fitting that couples said housing means to the dental instrument; and (c) a one-way valve disposed within said housing means, said one-way valve enabling fluid to flow into the patient's mouth, but preventing fluid flow in an opposite direction, so that oral reflux of contaminants from within the patient's mouth into the dental instrument does not occur.

2. The apparatus of claim 1, wherein the fluid is injected into the patient's mouth through a disposable tip for the dental instrument.

3. The apparatus of claim 2, wherein said housing means are formed integrally with the disposable tip, to be discarded after use with a patient.

4. The apparatus of claim 1, further comprising a bacteriological sterilization filter disposed within the housing means, said bacteriological sterilization filter including a microporous membrane having a porosity selected to block a predefined size of particulate matter, including bacteria, without substantially restricting fluid flow through the membrane.

5. The apparatus of claim 4, wherein said housing means comprise a filter housing and a valve housing; and wherein said bacteriological sterilization filter is disposed within the filter housing, and said one-way valve is disposed within the valve housing, said filter housing and said valve housing being separate from each other.

6. The apparatus of claim 4, wherein at least a portion of the membrane is coated with a hydrophobic material, said fluid passing through said portion of the membrane.

7. The apparatus of claim 1, wherein the fluid flowing through the housing means comprises water.

8. The apparatus of claim 1, wherein the fluid flowing through the housing means comprises compressed air.

9. The apparatus of claim 1, wherein dental instrument comprises a syringe having a removable tip through which the fluid is injected into the patient's mouth, said housing means including a quick-connect fitting on said at least one outlet port of the housing, to couple to the removable tip.

* * * * *